(12) United States Patent
McKibben (10) Patent No.: US 7,824,668 B2
(45) Date of Patent: Nov. 2, 2010

(54) COMPOSITIONS FOR ATTRACTING STINK BUGS

(75) Inventor: Gerald H. McKibben, Starkville, MS (US)

(73) Assignee: Cotton Incorporated, Cary, NC (US)

( * ) Notice: Subject to any disclaimer, the term of this patent is extended or adjusted under 35 U.S.C. 154(b) by 361 days.

(21) Appl. No.: 11/774,424

(22) Filed: Jul. 6, 2007

(65) Prior Publication Data

US 2008/0044375 A1 Feb. 21, 2008

Related U.S. Application Data

(60) Provisional application No. 60/830,653, filed on Jul. 12, 2006.

(51) Int. Cl.
*A01N 25/00* (2006.01)
*A01M 1/10* (2006.01)
*A01M 5/00* (2006.01)

(52) U.S. Cl. .............................. 424/84; 424/405; 43/58; 43/132.1

(58) Field of Classification Search ........................ None
See application file for complete search history.

(56) References Cited

U.S. PATENT DOCUMENTS

| | | | |
|---|---|---|---|
| 5,447,718 A | 9/1995 | Aldrich et al. | |
| 6,054,141 A | 4/2000 | Mayer et al. | |
| 6,183,733 B1 | 2/2001 | McKibben | |
| 6,218,416 B1 | 4/2001 | Sembo | |
| 6,306,416 B1 | 10/2001 | McKibben et al. | |
| 6,316,017 B1 | 11/2001 | McKibben et al. | |
| 6,387,933 B1 | 5/2002 | Nakamura et al. | |
| 6,413,508 B1 | 7/2002 | Dickens | |
| 2003/0060379 A1 | 3/2003 | Souter et al. | |
| 2008/0044375 A1* | 2/2008 | McKibben | .................. 424/84 |

OTHER PUBLICATIONS

Harrewijn et al. (Chemoecology. 1995; 5/6(2): 55-73).*
Taylor (Veterinary Journal. 2001; 161(3): 253-68).*
Aldrich et al. (Journal of Chemical Ecology. 1995; 21(12): 1907-1920).*
Dudareva et al. (Plant Physiology. Aug. 2004. 135: 1893-1902).*
Ruther, J., et al., "Attraction of garden chafer, *Phyllopertha horticola*, to floral Japanese beetle lure." J. Appl. Ent. (2004) vol. 128, pp. 158-160.
Aldrich, J. R., et al., "Identification and attractiveness of a major pheromone component for nearctic *Euschistus* spp. stink bugs . . . " Environ. Ent. (1991) vol. 20 (2), pp. 477-483.
Ho, H., et al., "Semiochemicals from the predatory stink bug *Eocanthecona furcellata* (Wolff): Components of metathoracic gland, dorsal abdominal gland, and sternal gland secretions." J. Chem. Ecol. (2003) vol. 29 (9), pp. 2101-2114.
Groot, A.T., et al., "Sex-related perception of insect and plant volatiles in *Lygocoris pabulinus*." J. Chem. Ecol. (1999) vol. 25 (10), pp. 2357-2371.
Aldrich, J. R., et al., "Identification of presumed pheromone blend from Australasian predaceous bug, *Oechalia schellenbergii*. . . " J. Chem. Ecol. (1996) vol. 22 (4), pp. 729-738.
Krupke, C.H., et al., "Field attraction of the stink bug *Euschistus conspersus* (Hemiptera: Pentatomidae) to synthetic pheromone . . . " J. Econ. Entomol. (2001) vol. 94 (6), pp. 1500-1505.
Borges, M., et al., "Field responses of stink bugs to the natural and synthetic pheromone of the Neotropical brown stink bug . . . " Physiological Entomology (1998) vol. 23, pp. 202-207.
Leskey, T.C., et al., "Monitoring stink bugs (Hemiptera: Pentatomidae) in mid-atlantic apple and peach orchards." J. Econ. Entomol. (2005) vol. 98 (1), pp. 143-153.

* cited by examiner

*Primary Examiner*—Shanon A Foley
(74) *Attorney, Agent, or Firm*—Sonnenschein Nath & Rosenthal LLP (57) ABSTRACT

The invention provides compositions for attracting stink bugs, which include at least one pheromone and at least one synergist. The synergist is a naturally-occurring phytochemical compound. The pheromone is preferably methyl (2E,4Z)-decadienoate, ethyl (2E,4Z)-decadienoate, methyl (2Z,4E)-decadienoate, or methyl (2E,4E)-decadienoate and the synergist is preferably geraniol. The invention also provides traps containing the composition for attracting stink bugs, and methods for attracting, capturing, killing or sterilizing stink bugs using the composition.

47 Claims, 7 Drawing Sheets

COMPOSITIONS FOR ATTRACTING STINK BUGS

RELATED APPLICATIONS

This application claims priority to provisional U.S. application No. 60/830,566, filed Jul. 12, 2006, the contents of which are incorporated by reference herein in their entirety.

FIELD OF THE INVENTION

The invention is directed to novel compositions and methods using these novel compositions for attracting stink bugs, particularly brown stink bugs.

BACKGROUND OF THE INVENTION

Stink bugs are pests which attack several economically important crops, including cotton, soybeans, pecans, plums and okra. Although a variety of chemical pesticides have been used in the past to control stink bugs, there are serious disadvantages in these pesticides. Some pesticides pollute the environment while others are toxic to humans. Such environmental and consumer safety concerns have led to the deregistration of many pesticides. Also, there is generally a reluctance to use any pesticides on agricultural products which are consumed as food. Therefore, eliminating, or at least reducing the amount of toxic pesticides used in the management of insect pests is desirable. Consequently, scientists have pursued the development of alternative pest control agents that are safer for the environment and for consumers. Among such alternative control agents are insect sex pheromones.

Many insects communicate by releasing volatile pheromones. Sex pheromones, for example, are typically released by one sex at appropriate times to attract the other sex of the same species. This phenomenon has been exploited to trap the insects of one sex and kill them, thereby preventing mating and reducing the insect population in following generations. Pheromones have been used in this way on a commercial basis for several years, and provide effective control of numerous insect pest species. For stink bugs, the ability to control the population was improved by the identification of the pheromone, methyl (2E,4Z)-decadienoate (Aldrich et al. *Environ. Entomol.* 20:477-483, 1991).

Although the use of pheromones is advantageous, most pheromones are artificially synthesized, and thus are very expensive. As a result, pest control or pest management using synthetic pheromones is not always cost efficient. In some cases, naturally occurring and less-expensive compounds can be identified that act as synergists to synthetic pheromones. For example, eugenol, a naturally occurring compound, has been identified as a synergist and is used with the synthetic pheromone, grandlure, for capturing and controlling cotton boll weevils. The naturally-occurring compound adds to the attractant effect of the grandlure (McKibben et al., U.S. Pat. No. 6,183,733).

To date, no such synergists, have been identified for pheromones of stink bugs. Accordingly, there exists a need to identify synergists for stink bug pheromones and develop less-expensive attractant formulations.

SUMMARY OF THE INVENTION

The invention provides synergists for stink-bug pheromones, and attractant-compositions for attracting stink bugs, which comprise pheromones and synergists. The attractant-composition attracts insects of one or more species of the genus *Euchistus* including, but not limited to, brown stink bugs.

The attractant-compositions contain at least one pheromone and at least one synergist for attracting stink bugs. In preferred embodiments, the pheromone can be an alkyl ester of (2E,4Z)-decadienoic acid such as methyl (2E,4Z)-decadienoate, ethyl (2E,4Z)-decadienoate, methyl (2Z,4E)-decadienoate, and methyl (2E,4E)-decadienoate (See U.S. Pat. No. 5,447,718), and combinations thereof, and the synergist may be, for example, geraniol or any other phytochemical insect attractant able to act as a synergist for attracting stink bugs. In some embodiments, the attractant-composition further contains one or more additives such as, for example, pesticides, insect sterilants and/or insect growth regulators. The attractant-compositions may incorporate inert additives and carriers, and be in the form of a liquid, pellets, microspheres, nanoparticles, tubules or combinations thereof.

The invention also provides traps for capturing stinkbugs, which include one or more septa or containers for holding the attractant-composition.

The invention provides a method for attracting and trapping stink bugs, thereby protecting crop plants from stink bugs. The method comprises the steps of attracting stink bugs with an attractant-composition of the invention; trapping the stink bugs; and killing or sterilizing the trapped stink bugs. Crop plants protected in this manner include, but are not limited to, cotton, soybean, plum, pecan, peach and okra.

In some embodiments, the method may include an additional step of assessing the population of trapped stink bugs. Such assessments may help, periodically, to monitor the stink bug population in a crop field.

Other features and advantages of the present invention will become apparent from the following detailed description. It should be understood, however, that the detailed description and the specific examples, while disclosing the preferred embodiments of the invention, are given by way of illustration only, and that various changes and modifications apparent to those skilled in the art are within the spirit and scope of the invention and the appended claims.

DETAILED DESCRIPTION OF THE INVENTION

The attractant-compositions of the invention contain at least two compounds. The first compound is a pheromone and the second compound is a synergist, as defined herein. The term "pheromone," as used herein, means a volatile chemical or a set of volatile chemicals that attract stink bugs.

In some embodiments, the pheromone is a sex pheromone which attracts one sex of stink bugs. In some embodiments, the pheromone is an alkyl ester. In particular embodiments, the pheromone is selected from the group methyl (2E,4Z)-decadienoate, ethyl (2E,4Z)-decadienoate, methyl (2Z,4E)-decadienoate, methyl (2E,4E)-decadienoate, and combinations thereof. In a preferred embodiment, the pheromone is methyl (2E,4Z)-decadienoate or an isomer thereof. The pheromone may be naturally occurring or chemically synthesized by methods known to one skilled in the art.

The term, "synergist," as used herein, refers to a substance that can be used with a stink bug pheromone for reducing the amount of the pheromone dose or enhancing the effectiveness of the pheromone for attracting stink bugs. The synergist may or may not be an independent attractant for stink bugs in the absence of a pheromone.

In preferred embodiments, the synergist is a volatile phytochemical that attracts stink bugs. The term, "phytochemical," as used herein, means a compound occurring naturally in a plant species.

In a particular embodiment, the synergist is geraniol (E-(3, 7)-Dimethyl-2,6-octadien-1-ol, $C_{10}H_{18}O$) or its Z isomer.

The attractant-composition may contain the pheromone and the synergist in a mixed or otherwise combined form or it may contain the pheromone and the synergist independently in non-mixed form.

The attractant-compositions may include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, malathion, and sevin.

In another embodiment, the insecticides are one or more biological insecticides known to one skilled in the art. Examples of the biological insecticides include, but are not limited to, toxins from natural pyrethrins, *Bacillus thuringiencis* and *Beauveria bassiana*.

In certain embodiments, the attractant-composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof. Examples of celluloses include, but are not limited to, methylcellulose, ethyl cellulose, cellulose acetate, cellulose acetate-butyrate, cellulose acetate-propionate, cellulose propionate, and combinations thereof.

According to another embodiment of the invention, the attractant-composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the invention, the attractant-composition may include one or more insect growth regulators ("IGRs"). IGRs may be used to alter the growth of the stink bugs and produce deformed stink bugs.

According to another embodiment of the invention, the attractant-composition may include one or more insect sterilants that sterilize the trapped insects or otherwise block their reproductive capacity, thereby reducing the population in the following generation. In some situations, allowing the sterilized insects to survive and compete with non-trapped insects for a mate is more effective than killing them outright.

According to another embodiment of the invention, the attractant-composition may include one or more additives that enhance the stability of the composition. Examples of additives include, but are not limited to, fatty acids and vegetable oils such as for example olive oil, soybean oil, corn oil, safflower oil, canola oil, and combinations thereof.

Furthermore, according to another embodiment of the invention, the attractant-composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

According to another embodiment, the attractant-compositions of the present invention include one or more solvents. Compositions containing solvents are desirable when a user is to employ liquid compositions which may be applied by brushing, dipping, rolling, spraying, or otherwise applying the liquid compositions to substrates on which the user wishes to provide an insecticidal coating. In some embodiments, the solvent(s) to be used in the instant invention is/are selected so as to solubilize, or substantially solubilize, the one or more ingredients of the attractant-composition. Examples of solvents include, but are not limited to, ethyl alcohol, methyl alcohol, chlorinated hydrocarbons, petroleum solvents, turpentine, xylene, and any combinations thereof.

According to another embodiment of the invention, the attractant-composition may include one or more binders, such as synthetic and natural resins typically used in paints and coatings. These may be modified to cause the coated surface to be friable enough to allow insects to bit off and ingest the material, while still maintaining the structural integrity of the coating. In some embodiments, the binder also acts as a filler and/or a thickener. Examples of binders include, but are not limited to, one or more of shellac, acrylics, epoxies, alkyds, polyurethanes, linseed oil, tung oil, and any combinations thereof.

The attractant-compositions of the invention may be used in traps, such as those commonly used to attract stink bugs. Such traps are well known to one skilled in the art, and are commonly used in many states and countries in their stink bug eradication programs. In one embodiment, the trap includes one or more septa, containers or storage receptacles for holding the attractant-composition. In some embodiments, the pheromone traps containing the attractant-composition may he combined with other kinds of trapping mechanisms. For example, in addition to the attractant-composition, the pheromone trap may include one or more florescent lights, one or more sticky substrates and/or one or more colored surfaces for attracting stink bugs. In other embodiments, the pheromone trap containing the attractant-composition may not have other kinds of trapping mechanisms. In particular embodiments, the trap is a Tedders trap (See e.g., Stansly et al., Proc. Fla. State Hort. Soc. 110: 22-26 (1997)) or a Florida trap (See e.g., Mizell and Tedders, Proc. Southeast Pecan Growers Assoc. 90: 52-53) as known to one skilled in art.

A plurality of traps containing the attractant-composition may be placed in a crop field. The locations of traps, and height of the traps from ground may be selected in accordance with methods known to one skilled in the art.

The attractant-composition attracts stink bugs. In one embodiment, the attractant-composition attracts insects of one or more species of the genus *Euschistus*. Examples of the *Euschistus* species include, but are not limited to, *E. servus, E. tristigmus, E. conspersus, E. variolarius, E. politus*, and *E. heros*. In a particular embodiment, the attractant-composition attracts brown stink bugs, for example, *E. servus*.

The invention also provides a method for attracting and trapping stink bugs. The method includes administering to a predetermined site an effective amount of the attractant-composition. Such administering may be performed by adding the attractant-composition to a septa or storage receptacle of a trap described herein. The trap may be set at any time of the year in a field. Those of skill in the art can readily determine an appropriate amount of the compositions to use in a particular trap, and can also determine an appropriate density of traps/acre of crop field to be protected.

The method may include periodically monitoring the total number or quantity of the trapped insects. The monitoring may be performed by counting the number of insects trapped for a predetermined period of time such as, for example, daily, weekly, bi-weekly, monthly, once-in-three months, or any time period selected by the monitor. Such monitoring of the trapped insects may help estimate the population of insects for that particular period, and thereby help determine a particular type and/or dosage of pest control in an integrated pest management system. For example, when the number of trapped stink bugs is more than a pre-determined level in a particular week, a chemical pesticide may be sprayed or applied to a crop field in order to control stink bugs or a higher concentration of traps/acre may be set in a crop field in order to control stink bugs during that particular week.

In some embodiments, the method includes adding a pesticide to the trap so as to kill the trapped stink bugs. The pesticide may be a pesticide known to one skilled in the art. The pesticide may be mixed with the attractant-composition or may be separately present in a trap. Mixtures may perform the dual function of attracting and killing the stink bugs.

The attractant-composition may be used in the fields of any crop plants. Examples of such crop plants include, but are not limited to, cotton, soybeans, plums, pecans, peaches and okra.

The following examples are provided to further illustrate the invention described herein.

EXAMPLES

Example 1

*Euschistus Tristigmus* Response to a Pheromone Synergist

An experiment was carried out near Starkville, Oktibbeha County in Mississippi to study the response of *Euschistus tristigmus* in a crop field to a pheromone synergist. The crop field was a soybean field bordered on two sides by woods. Geraniol was used as a synergist with methyl (2E,4Z)-decadienoate, a pheromone for *Euschistus tristigmus*. Tedders traps were used in the experiment. Each trap was baited with 160 mg geraniol and 200 mg methyl (2E,4Z)-decadienoate and each control trap was baited with 200 mg methyl (2E,4Z)-decadienoate. The control trap contained no geraniol or other synergists. The trapped adult insects of *Euschistus tristigmus* were collected on a daily basis and the total number of trapped insects was counted. Statistical analysis was done using the Least Squares means separation from the SAS GLM procedure.

Figure 1:
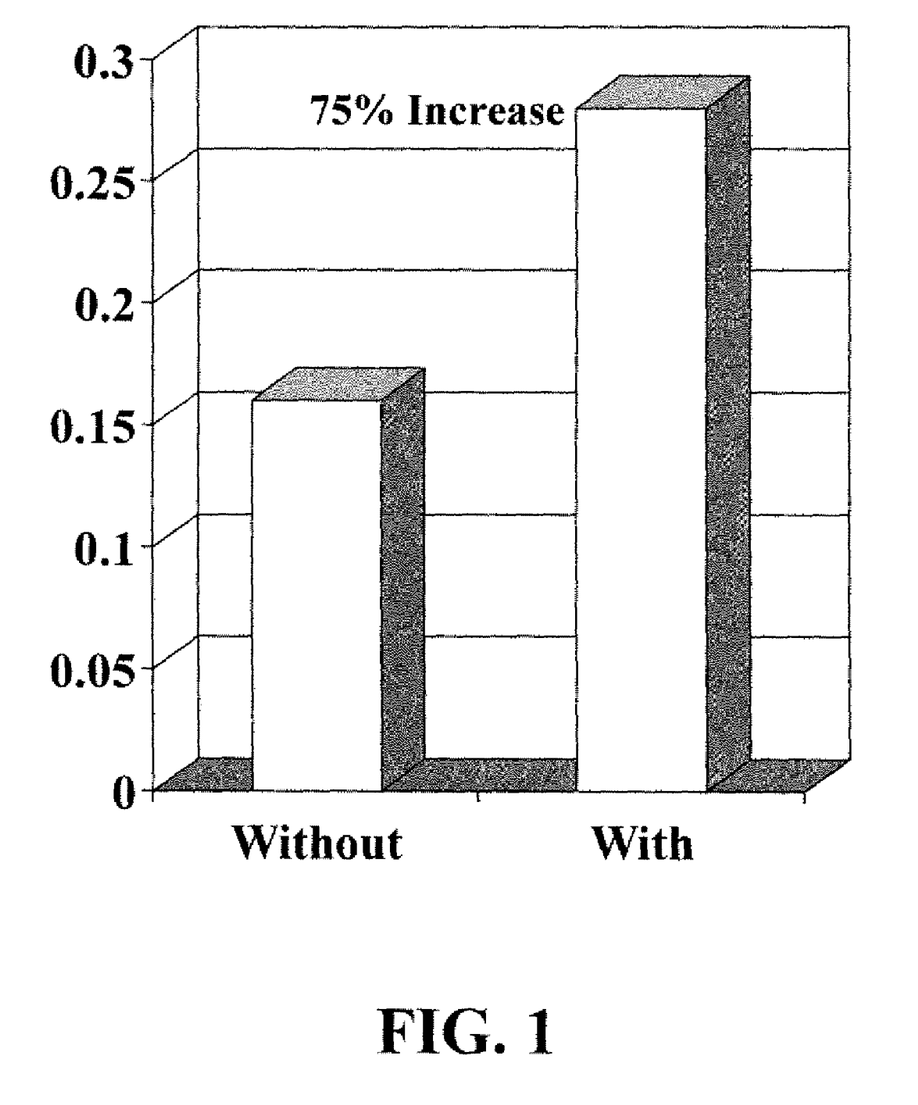
FIG. 1 illustrates a response of *Euchistus tristigmus* in a soybean field to pheromone compositions with and without geraniol as a synergist.

FIG. 1 illustrates the average number of bugs trapped per day. As illustrated in FIG. 1, there was about a 75% increase in the number of captured *Euschistus tristigmus* when geraniol was used as a synergist. The observed increase in captured bugs was statistically significant at Pr>t 0.04 (1,232 df).

Accordingly, methyl (2E,4Z)-decadienoate, when used with geraniol, significantly improved the trap captures. Thus, geraniol acts as a synergist with methyl (2E,4Z)-decadienoate to attract *Euschistus tristigmus*.

Example 2

*Euschistus Servus* Response to a Pheromone Synergist

An experiment was carried out near Starkville, Oktibbeha County in Mississippi to study the response of *Euschistus servus* to a pheromone synergist. Geraniol was used as a synergist with methyl (2E,4Z)-decadienoate, a pheromone for *Euschistus servus*. Tedders traps were used in the experiment. Each treatment trap was baited with 160 mg geraniol and 200 mg methyl (2E,4Z)-decadienoate and each control trap was baited with 200 mg methyl (2E,4Z)-decadienoate. The control trap contained no geraniol or any other synergist. The trapped adult insects of *Euschistus servos* were collected on a daily basis and their total numbers were counted. Statistical analysis was done using the Least Squares means separation from the SAS GLM procedure.

Figure 2:
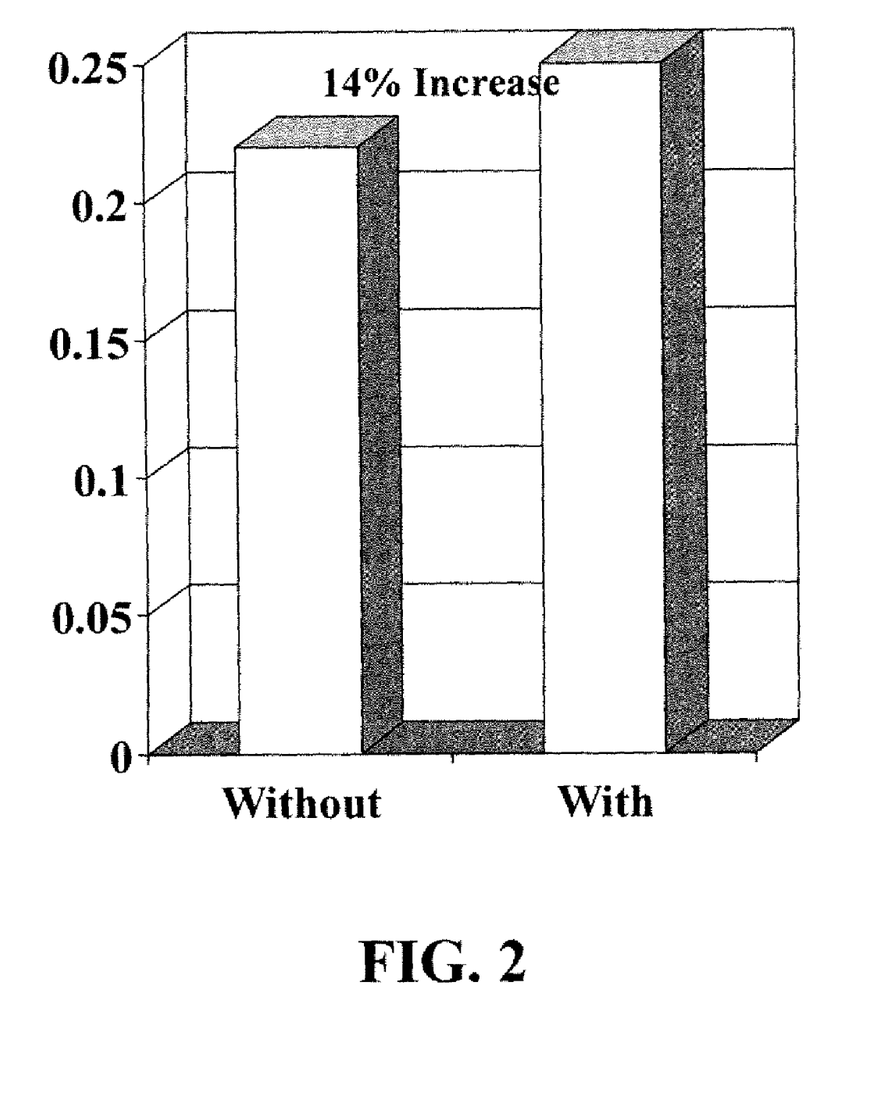
FIG. 2 illustrates a response of *Euchistus servus* in a soybean field to pheromone compositions with and without geraniol as a synergist.

FIG. 2 illustrates the average number of bugs trapped per day in soybean field. As illustrated in FIG. 2, there was about a 14% increase in the number of captured bugs when geraniol was used as a synergist. The observed increase in captured bugs was statistically significant at Pr>t 0.61 (1,232 df).

Figure 3:
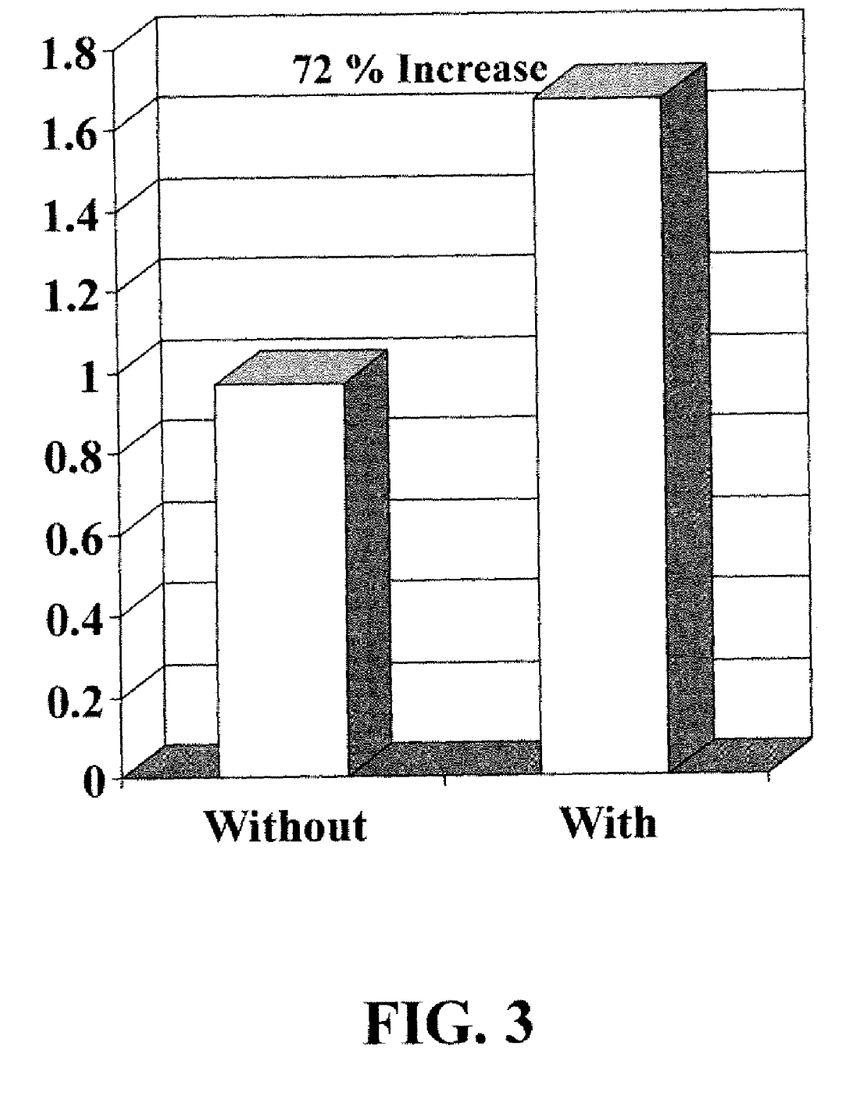
FIG. 3 illustrates a response of *Euchistus servus* in a crepe myrtle field to pheromone compositions with and without geraniol as a synergist.

FIG. 3 illustrates the average number of bugs trapped per day in a crepe myrtle field. As illustrated in FIG. 3, there was about a 72% increase in the number of captured bugs when geraniol was used as a synergist. The observed increase in captured bugs was statistically significant at Pr>t 0.51 (2.27 df).

Figure 4:
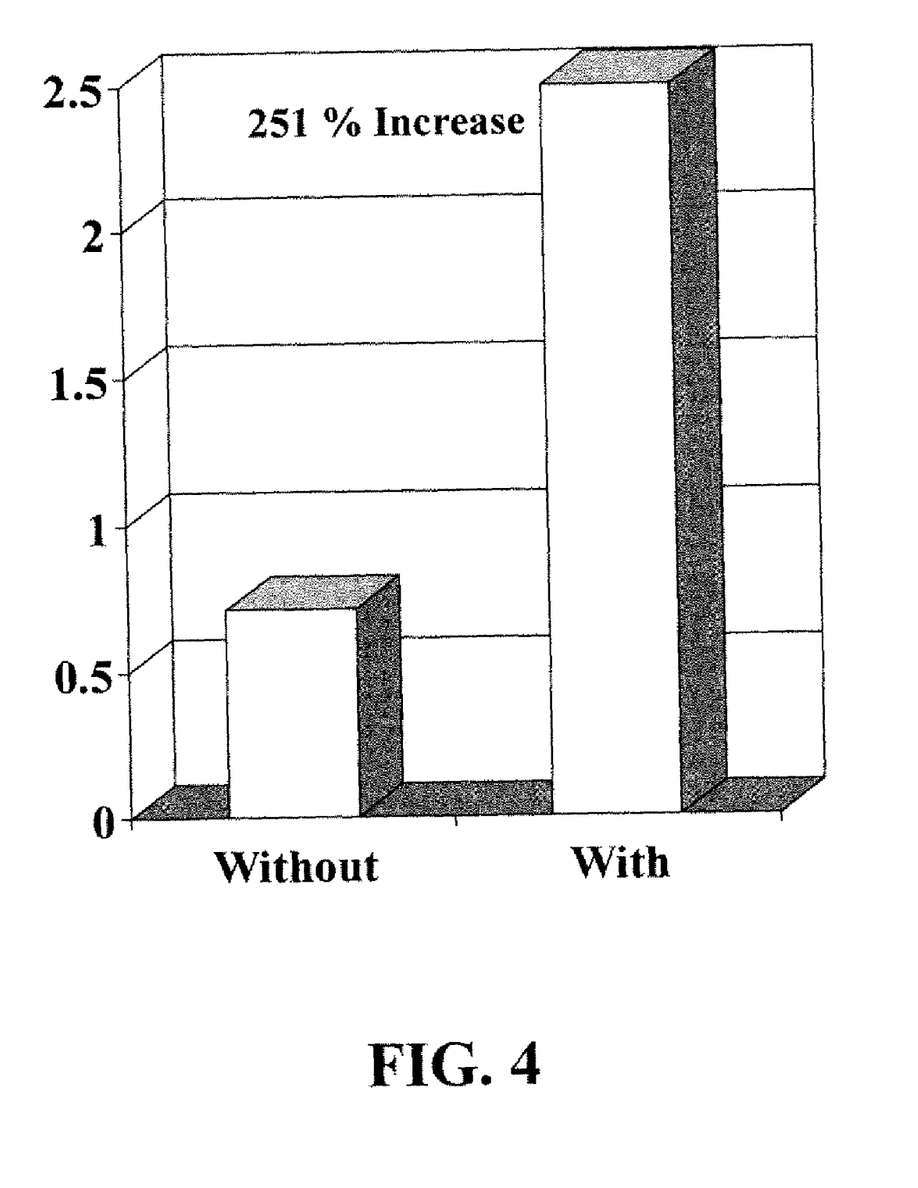
FIG. 4 illustrates a response of *Euchistus servus* in a new peach field to pheromone compositions with and without geraniol as a synergist.

FIG. 4 illustrates the average number of bugs trapped per day in a new-peach field. As illustrated in FIG. 4, there was about a 251% increase in the number of captured bugs when geraniol was used as a synergist. The observed increase in captured bugs was statistically significant at Pr>t 0.05 (2.27 df).

Figure 5:
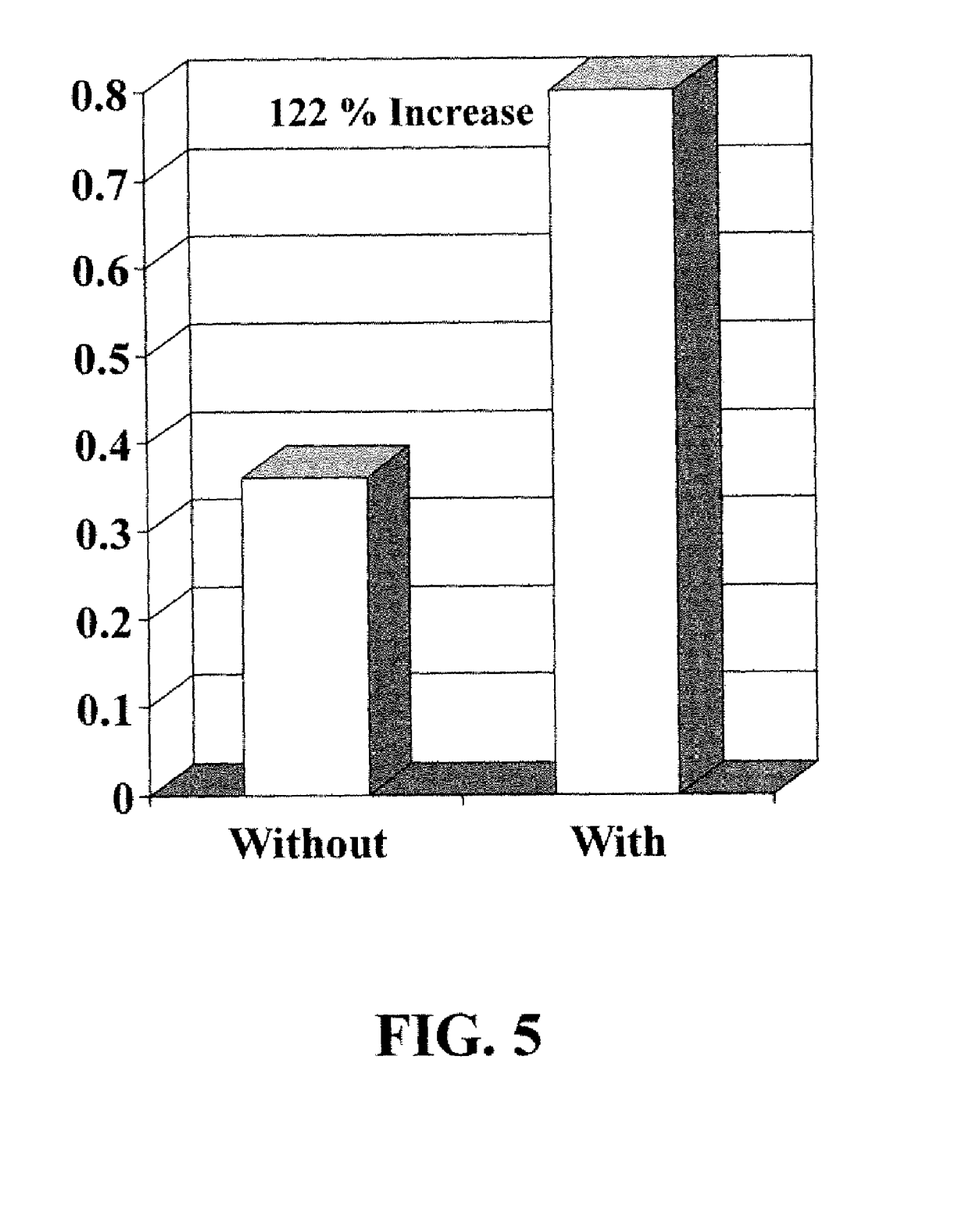
FIG. 5 illustrates a response of *Euchistus servus* in a old peach field to pheromone compositions with and without geraniol as a synergist.

FIG. 5 illustrates the average number of bugs trapped per day in an old-peach field. As illustrated in FIG. 5, there was about a 122% increase in the number of captured bugs when geraniol was used as a synergist. The observed increase in captured bugs was statistically significant at Pr>t 0.02 (2.57 df).

Figure 6:
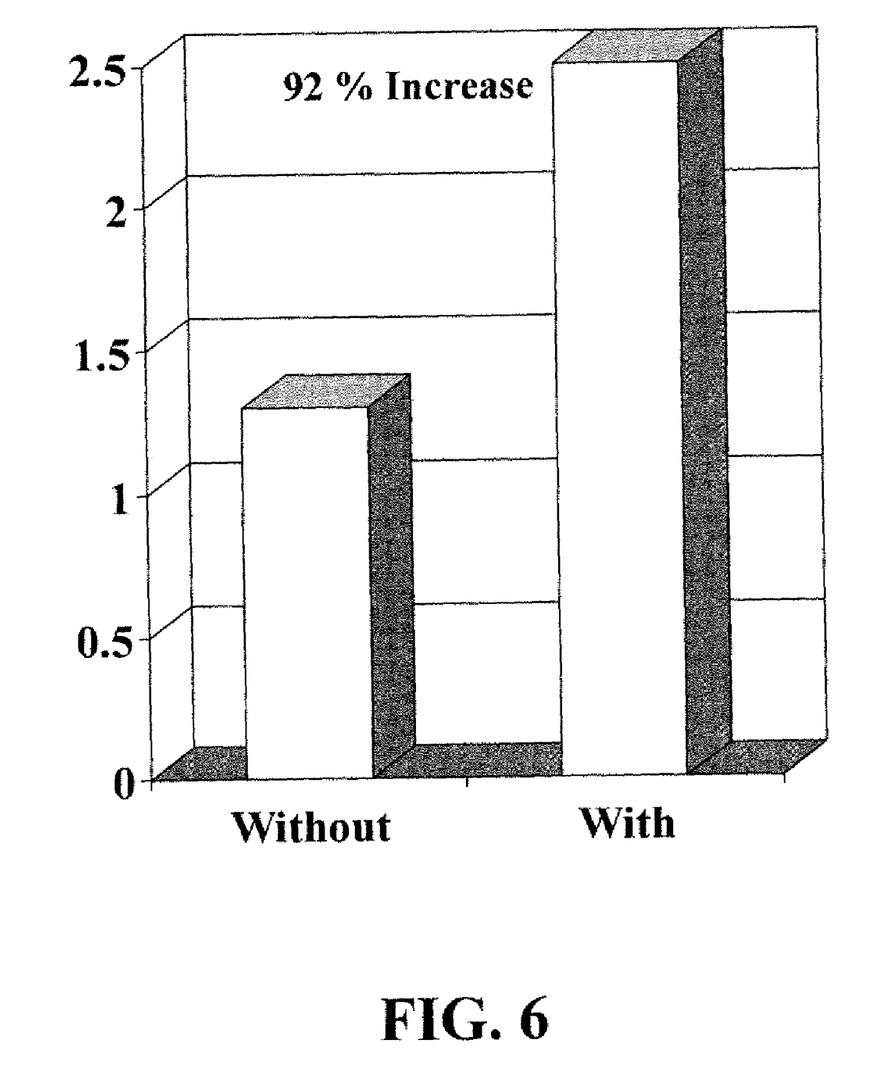
FIG. 6 illustrates a response of *Euchistus servus* in a mixed crop field to pheromone compositions with and without geraniol as a synergist.

FIG. 6 illustrates the average number of bugs trapped per day in a field of mixed crops of plum and okra. As illustrated in FIG. 6, there was about a 92% increase in the number of captured bugs when geraniol was used as a synergist. The observed increase in captured bugs was statistically significant at Pr>t 0.02 (2.57 df).

Accordingly, methyl (2E,4Z)-decadienoate, when used with geraniol, significantly improved the trap captures. Thus, geraniol acts as a synergist with methyl (2E,4Z)-decadienoate for attracting *Euschistus servus*.

Example 3

*Euschistus* Species Response to a Pheromone Synergist

An experiment was carried out in Monticello, Ark. to study the response of *Euschistus* species in a soybean field to a pheromone synergist. Geraniol was used as a synergist to methyl (2E,4Z)-decadienoate, which is a pheromone for both *Euschistus* species. Tedders traps were used in the experiment. Each treatment trap was baited with 160 mg geraniol and 200 mg methyl (2E,4Z)-decadienoate and each control trap was baited with 200 mg methyl (2E,4Z)-decadienoate. The control traps contained no geraniol or any other synergist. The trapped adult insects of *Euschistus* species were collected on a daily basis and their total numbers were counted. Statistical analysis was done using the Least Squares means separation from the SAS GLM procedure.

Figure 7:
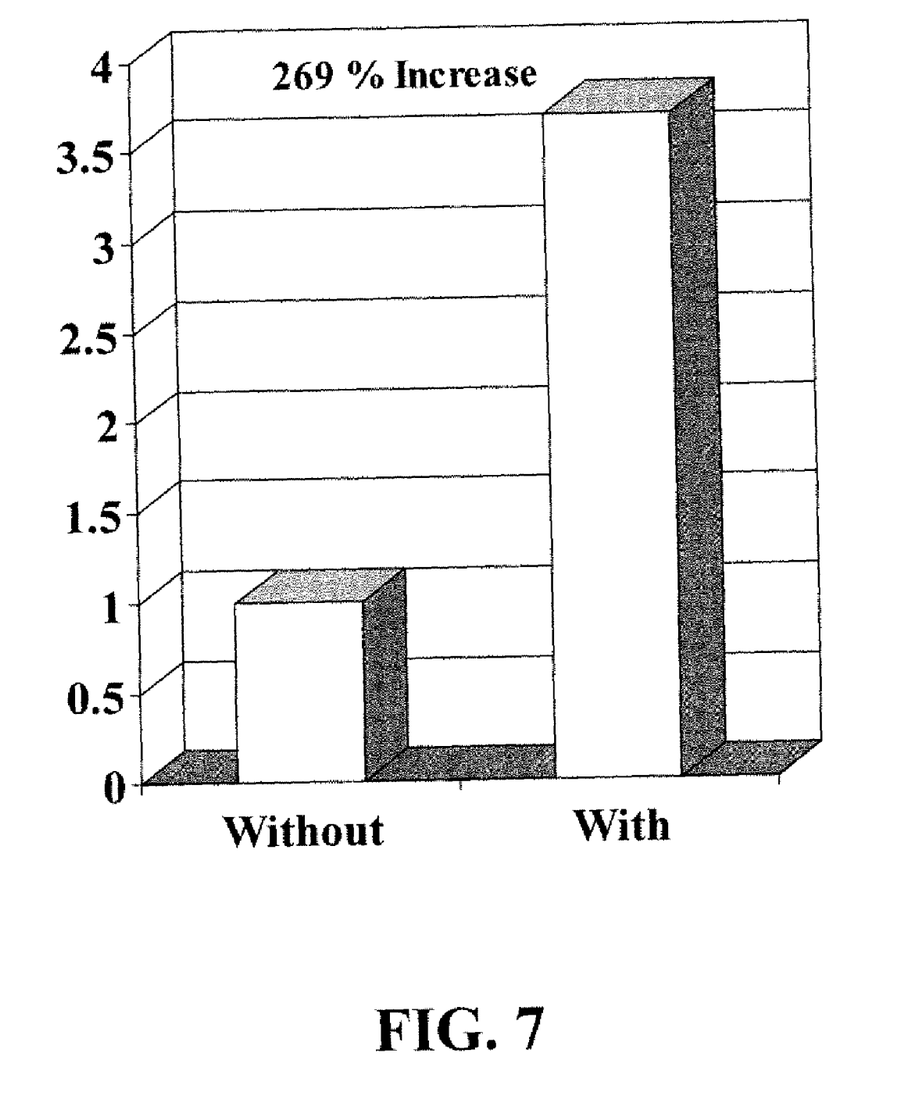
FIG. 7 illustrates a response of *Euchistus* spp. in a soybean field to pheromone compositions with and without geraniol as a synergist.

FIG. 7 illustrates the average number of bugs trapped per day. As illustrated in FIG. 7, there was about a 269% increase in the number of captured bugs when geraniol was used as a synergist. The observed increase in captured bugs was statistically significant at Pr>t 0.09 (1,31 df).

Accordingly, methyl (2E,4Z)-decadienoate, when used with geraniol, significantly improved the trap captures. Thus, geraniol acts as a synergist with methyl (2E,4Z)-decadienoate to attract *Euschistus* species in a soybean field.

All publications and patents cited above are hereby incorporated by reference.

What is claimed is:

1. A composition comprising:
   at least one pheromone compound that attracts at least one species of the genus *Euschistus*; and
   at least one synergist compound,
   wherein said at least one pheromone compound is (a) an alkyl ester of (2E,4Z)-decadienoate, (b) methyl (2Z,4E)-decadienoate, (c) methyl (2E,4E)-decadienoate or (d) ethyl (2E,4Z)-decadienoate, and said at least one synergist compound is geraniol.

2. The composition of claim 1, wherein said at least one pheromone compound is, ethyl (2E,4Z)-decadienoate.

3. The composition of claim 1, wherein said at least one pheromone compound is methyl (2E,4Z)-decadienoate.

4. The composition of claim 1, wherein from about 50 mg to about 300 mg of the pheromone compound is present in the composition.

5. The composition of claim 1, wherein from about 100 mg to about 200 mg of the pheromone compound is present in the composition.

6. The composition of claim 1, wherein about 50, 75, 100, 150, 175, 200, 250 or 300 mg of the pheromone compound is present in the composition.

7. The composition of claim 1, wherein from about 10 mg to about 200 mg of geraniol is present in the composition.

8. The composition of claim 1, wherein from about 50 mg to about 160 mg of geraniol is present in the composition.

9. The composition of claim 1, wherein about 10, 20, 30, 50, 75, 100, 150, 160, 175 or 200 mg of geraniol is present in the composition.

10. The composition of claim 1, wherein the at least one species is *Euschistus tristigmus*.

11. The composition of claim 1, wherein the at least one species is *Euschistus servus*.

12. The composition of claim 1, wherein the composition further comprises a pesticide.

13. The composition of claim 1, wherein the composition further comprises an insect growth regulator.

14. The composition of claim 1, wherein the composition further comprises an insect sterilant.

15. The composition of claim 1, wherein the composition is in the form of a pellet, microspheres, nanoparticles or tubules.

16. The composition of claim 1, wherein the composition is in a storage receptacle of a trap for capturing an insect.

17. The composition of claim 1, wherein about 200 mg of the pheromone compound is present in the composition.

18. The composition of claim 1, wherein about 200 mg of methyl (2E,4Z)-decadienoate is present in the composition.

19. The composition of claim 1, wherein about 160 mg of geraniol is present in the composition.

20. The composition of claim 1, wherein about 200 mg of methyl (2E,4Z)-decadienoate and 160 mg of geraniol is present in the composition.

21. A method for controlling at least one species of the genus *Euschistus* comprising:
   administering to a predetermined site an effective amount of the composition of claim 1.

22. The method of claim 21, further comprising periodically monitoring the at least one species of the genus *Euschistus* captured at the predetermined site.

23. The method of claim 22, the step of monitoring comprising collecting the captured species of the genus *Euschistus* at the predetermined site and counting the total number of the captured species of the genus *Euschistus*.

24. The method of claim 21, wherein said at least one pheromone compound is methyl (2E,4Z)-decadienoate.

25. The method of claim 21, wherein the concentration of pheromone compound ranges from about 50 mg to about 300 mg.

26. The method of claim 21, wherein the concentration of pheromone compound ranges from about 100 mg to about 200 mg.

27. The method of claim 21, wherein the concentration of pheromone compound is about 50, 75, 100, 150, 175, 200, 250 or 300 mg.

28. The method of claim 21, wherein said at least one synergist compound is geraniol.

29. The method of claim 21, wherein the concentration of synergist compound ranges from about 10 mg to about 200 mg.

30. The method of claim 21, wherein the concentration of synergist compound ranges from about 50 mg to about 160 mg.

31. The method of claim 21, wherein the concentration of synergist compound is about 10, 20, 30, 50, 75, 100, 150, 160, 175 or 200 mg.

32. The method of claim 21, wherein the at least one species is *Euschistus tristigmus*.

33. The method of claim 21, wherein the at least one species is *Euschistus servus*.

34. The method of claim 21, wherein the composition further comprises a pesticide.

35. The method of claim 21, wherein the composition further comprises an insect growth regulator.

36. The method of claim 21, wherein the composition further comprises an insect sterilant.

37. The method of claim 21, wherein the composition is in the form of pellets, microspeheres, nanoparticles or tubules.

38. The method of claim 21, wherein the predetermined site is a field having a cotton crop.

39. The method of claim 21, wherein the predetermined site is a field having a soybean crop.

40. The method of claim 21, wherein the predetermined site is a field having a tree crop.

41. The method of claim 21, wherein the tree crop is a species of plum.

42. The method of claim 21, wherein the tree crop is a species of pecan.

43. The method of claim 21, wherein the tree crop is a species of peach.

44. The method of claim 21, wherein the predetermined site is a field having a vegetable crop.

45. The method of claim 44, wherein the vegetable crop is a species of okra.

46. A method for attracting at least one species of the genus *Euchistus* comprising:

administering to a predetermined site an effective amount of a composition for attracting at least one species of the genus *Euchistus*, the composition comprising at least one pheromone compound selected from the group comprising methyl (2E,4Z)-decadienoate, ethyl (2E,4Z)-decadienoate, methyl (2Z,4E)-decadienoate, and methyl (2E,4E)-decadienoate; and at least one synergist compound to said at least one pheromone compound, wherein said at least one synergist compound is geraniol.

47. A method for attracting at least one species of the genus *Euchistus* comprising:

administering to a predetermined site an effective amount of a composition attracting at least one species of the genus *Euchistus*, the composition comprising at least one pheromone compound and at least one synergist compound to said at least one pheromone compound wherein said at least one pheromone compound is methyl (2E,4Z)-decadienoate and said at least one synergist compound is geraniol.

* * * * *